United States Patent
Felix et al.

(10) Patent No.: US 12,269,658 B2
(45) Date of Patent: Apr. 8, 2025

(54) SEALED CONTAINER COMPRISING A DEVICE FOR RELEASABLE CONNECTION TO AN ENCLOSURE

(71) Applicant: ABC TRANSFER, Tours (FR)

(72) Inventors: Julien Felix, Vendome (FR); Jean-Luc Schneider, Saint Firmin des Pres (FR); Thierry Girard, Paris (FR)

(73) Assignee: ABC TRANSFER, Tours (FR)

( * ) Notice: Subject to any disclaimer, the term of this patent is extended or adjusted under 35 U.S.C. 154(b) by 167 days.

(21) Appl. No.: 17/774,627

(22) PCT Filed: Nov. 5, 2020

(86) PCT No.: PCT/FR2020/052007
§ 371 (c)(1),
(2) Date: May 5, 2022

(87) PCT Pub. No.: WO2021/089949
PCT Pub. Date: May 14, 2021

(65) Prior Publication Data
US 2022/0396403 A1    Dec. 15, 2022

(30) Foreign Application Priority Data
Nov. 5, 2019    (FR) ................... FR1912407

(51) Int. Cl.
*B65D 53/02*    (2006.01)
*B65D 51/24*    (2006.01)

(52) U.S. Cl.
CPC ............ *B65D 53/02* (2013.01); *B65D 51/24* (2013.01)

(58) Field of Classification Search
CPC ................................ B65D 53/02; B65D 51/24
(Continued)

(56) References Cited

U.S. PATENT DOCUMENTS 6,591,662 B1 * 7/2003 Grimard ............ G01M 3/2869
                                                            73/49.8
2002/0176639 A1 * 11/2002 Crawley ............ B65D 35/245
                                                            383/33
(Continued)

FOREIGN PATENT DOCUMENTS

CN    102740812      10/2012
CN    106586189      4/2017
(Continued)

OTHER PUBLICATIONS

Office Action for Chinese counterpart application (202080073611.2) issued Sep. 24, 2023.
(Continued)

*Primary Examiner* — Jes F Pascua
(74) *Attorney, Agent, or Firm* — McDonnell Boehnen Hulbert & Berghoff LLP

(57) ABSTRACT

The invention relates to a sealed container (1) comprising a flexible film (2) which is arranged to define an internal space (3) and a through-opening, and a sealed connection device (4) which is arranged to allow the flexible film (2) to be connected to a complementary connection device of a sterile enclosure, while ensuring sterile communication between the internal space (3) of the container (1) and that of the enclosure, the connection device (4) comprising a flange to which the flexible film (2) is attached, the flange delimiting the through-opening of the flexible film (2), characterized in that the flange is constituted by two different pieces distinct from each other, respectively forming an external sleeve (5) and an internal sleeve (6) the flexible film (2) being kept gripped between the external sleeve (5) and the internal sleeve (6).

15 Claims, 4 Drawing Sheets

(58) Field of Classification Search
USPC .......................................................... 383/60
See application file for complete search history.

(56) References Cited

U.S. PATENT DOCUMENTS

| | | | |
|---|---|---|---|
| 2005/0168117 A1* | 8/2005 | Porret | B01L 1/02 |
| | | | 312/291 |
| 2006/0110077 A1* | 5/2006 | Savage | B65D 77/067 |
| | | | 383/906 |
| 2012/0153610 A1 | 6/2012 | Young | |
| 2018/0369801 A1 | 12/2018 | Pallares et al. | |
| 2022/0371011 A1* | 11/2022 | Felix | G21F 5/12 |

FOREIGN PATENT DOCUMENTS

| | | | |
|---|---|---|---|
| CN | 109675079 A * | 4/2019 | |
| JP | 2000514760 | 4/1998 | |
| JP | 2005517594 | 8/2012 | |
| JP | 5497944 | 12/2014 | |

OTHER PUBLICATIONS

Office Action for Japanese counterpart application (2022-525585) issued Feb. 26, 2024.

* cited by examiner

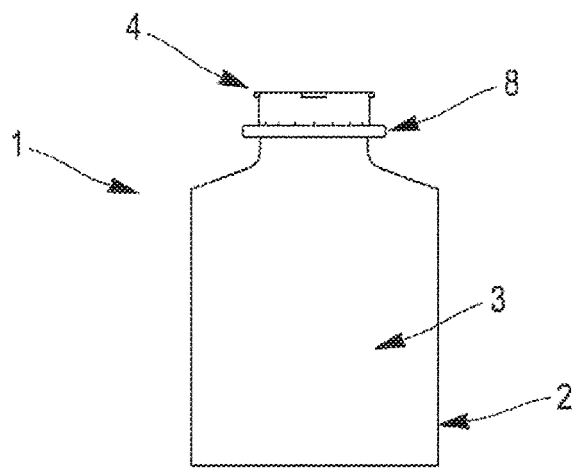
Fig. 1
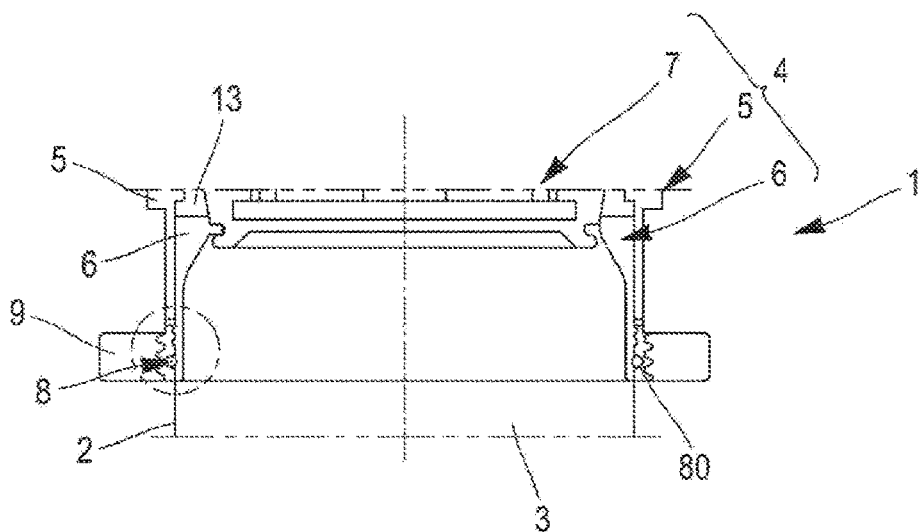
Fig. 2
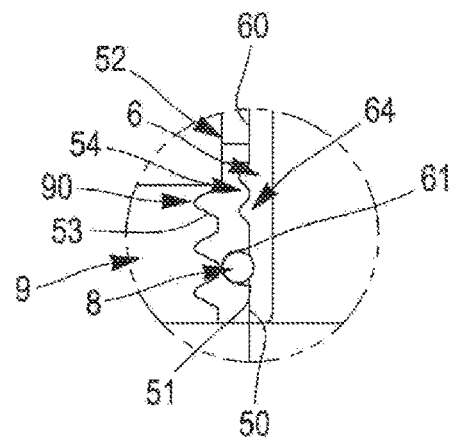
[Fig. 3]

SEALED CONTAINER COMPRISING A DEVICE FOR RELEASABLE CONNECTION TO AN ENCLOSURE

CROSS REFERENCE TO RELATED APPLICATION

This application is a U.S. National Phase of International Application No. PCT/FR2020/052007, filed Nov. 5, 2020, which claims priority to French Patent Application No. FR1912407, filed Nov. 5, 2019, both of which are incorporated by reference herein in their entirety.

TECHNICAL FIELD OF THE INVENTION

The invention relates to the field of containers intended to be connected in a sealed manner to sterile enclosures so as to allow their respective volumes to be placed in communication without contact with said external environment.

The invention relates more particularly to a sealed container comprising a flexible film arranged to define an internal space and a through-opening allowing the internal space to be placed in communication with the exterior of the film, and a sealed connection device arranged to allow the connection of the flexible film to a complementary connection device of a sterile enclosure.

The sealed container according to the invention is intended in particular, but not exclusively, for the transfer of dangerous products such as certain pharmaceutical, biotechnological, biological, chemical or radioactive products, the transfer of components such as stoppers, bottles, pistons, syringes, etc., the transfer of environmental control devices such as culture medium racks, particle counters, etc., the transfer of cleaning systems, the transfer of liquids, powders, tools, the transfer of waste to the outside of the enclosure and/or the transfer of any element necessary for the production or maintenance of the production line.

PRIOR ART

In a known manner, the connection of a sealed container to a sterile enclosure for the transfer of products, without breaking the connection and the seal, is carried out using two connection devices, one equipping the container and the other equipping the enclosure. Each connection device comprises a flange respectively delimiting the through-opening in the internal space of the container or of the enclosure, each of the through-openings being closed off by a door. The flange and the door of the container are capable of being connected respectively to the flange and to the door of the enclosure by a bayonet connection and separated from one another under the action of a rotational movement of the associated flange and door of the container with respect to the flange and door of the enclosure to which they are attached.

In the case of flexible film containers, the connection device and the flexible film are assembled by welding the film to the flange. Assembly by welding for this type of container, however, has a number of drawbacks.

Firstly, assembly by welding does not ensure optimal sealing and the presence of leak points cannot be ruled out. Similarly, a homogeneous weld cannot be guaranteed at all points on the surface of the film. Moreover, since welding intrinsically modifies the materials on which it is carried out, the flexible film may undergo an alteration during the welding operation, which can then generate points of fragility in terms of resistance and sealing.

Secondly, the junction device has the drawback of not being removable and therefore of not being recyclable.

Thirdly, assembly by welding dictates the materials used for the flange on which the film is welded and for the film itself.

The invention aims to remedy these problems by proposing a sealed container with a flexible film that can be connected to a sterile enclosure having improved mechanical strength and ensuring optimum sealing.

Another object of the invention is to provide a sealed container with a flexible film that can be connected to a sterile enclosure and that can be produced simply and quickly, without risk of deterioration of the film and of contamination.

Another object of the invention is to provide a sealed container with a recyclable flexible film.

SUBJECT MATTER OF THE INVENTION

To this end, the invention proposes a sealed container comprising a flexible film arranged to define an internal space and a through-opening, and a sealed connection device arranged to allow the flexible film to be connected to a complementary connection device of a sterile enclosure, while ensuring sterile communication between the internal space of said container and that of the enclosure, the connection device comprising a flange to which the flexible film is attached, said flange delimiting the through-opening of the flexible film, the container being remarkable in that the flange is constituted by two pieces distinct from each other, respectively forming an external sleeve and an internal sleeve the flexible film being kept gripped between the external sleeve and the internal sleeve.

The invention also proposes a sealed container comprising a flexible film arranged to define an internal space and a through-opening, a door closing off the through-opening as well as a sealed connection device arranged to allow the flexible film to be connected to a complementary connection device of a sterile enclosure by providing sterile communication between the internal space of said container and that of the enclosure, the connection device comprising a flange for assembling the door to the flexible film and means for connection to the complementary connection device of the enclosure, said assembly flange delimiting the through-opening of the flexible film, the container being remarkable in that the assembly flange is constituted by two pieces distinct from each other, respectively forming an external sleeve and an internal sleeve on which the door is mounted, the flexible film being kept gripped between the external sleeve and the internal sleeve.

According to other advantageous and non-limiting features of the invention, taken alone or in any technically practicable combination:
- the internal sleeve is surrounded in the lower part by the external sleeve and in the upper part by a collar arranged to ensure the connection to the complementary connection device of the enclosure, the collar forming said means for connecting the connection device.
- the container comprises first means for indexing the connecting collar with the internal sleeve.
- the container comprises second means for indexing the door with the internal sleeve.
- the external sleeve is mounted clipped onto the internal sleeve.

the external and internal sleeves are sized relative to one another so as to cause a gadroon provided on the external sleeve to bear on the internal sleeve.

the connection means to the complementary connection device of the enclosure are formed integrally with the external sleeve.

the container comprises means for clamping the external sleeve on the internal sleeve, arranged to grip the parts of the external sleeve and of the internal sleeve between which the flexible film is interposed.

the container comprises an annular seal housed in an internal peripheral groove of the external sleeve, the flexible film extending between the annular seal and the internal sleeve.

the internal sleeve has a face provided with a bearing recess located opposite the peripheral groove of the external sleeve.

the internal sleeve has a notched zone adjacent to the bearing recess arranged to cooperate with a complementary notching provided on the inner face of the external sleeve.

the external sleeve has a lower skirt comprising longitudinal slots extending from the lower end edge of the external sleeve and evenly distributed over the periphery of said sleeve so as to form elastic tabs capable of exerting a clamping force on the internal sleeve.

the elastic tabs comprise means of reciprocal association with the clamping means.

the connection device comprises a door mounted on the internal sleeve, closing the through-opening.

the flange comprises an annular seal having a substantially L-shaped section housed in an area delimited by the external sleeve, the internal sleeve and the door.

the flexible film and the connection device are made of a bacteriostatic material.

BRIEF DESCRIPTION OF THE DRAWINGS

Other features and advantages of the invention will become apparent from the following detailed description of the invention, which is provided with reference to the appended figures and in which:

FIG. 1 shows a schematic front view of a container according to the invention;

FIG. 2 shows a partial longitudinal sectional view of the container of FIG. 1;

FIG. 3 shows a detail view of the container of FIG. 2;

For greater clarity, identical or similar elements of the various embodiments are denoted by identical reference signs in all of the figures.

Figure 4:
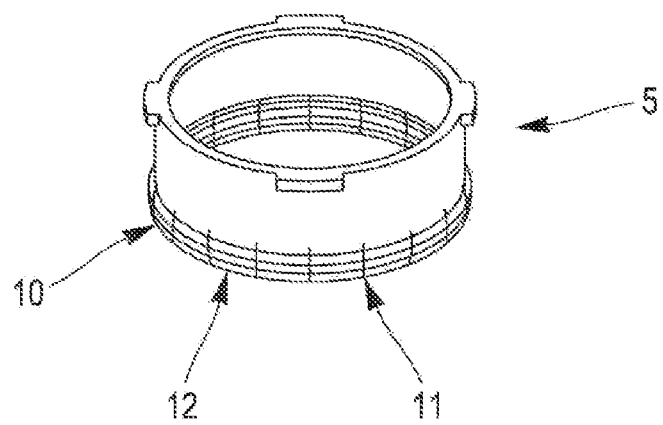
FIG. 4 shows a partial view of the external sleeve 5 of the connection device of the container of FIG. 2.

"Lower" means the parts constituting the container or the ends of these parts furthest from the through-opening of the container, and "upper" means the parts constituting the container or the ends of these parts closest to the through-opening of the container.

DETAILED DESCRIPTION OF THE INVENTION

In relation to FIGS. 1 to 5, a container 1 is described according to a first embodiment of the invention. The illustrated container 1 comprises a flexible film 2 arranged to define an internal space 3 and a through-opening allowing the internal space 3 to be placed in communication with the exterior of the film. The container also comprises a sealed connection device 4 that is arranged to allow the flexible film 2 to be connected to a complementary connection device of a sterile enclosure. The connection is made in such a way as to ensure sterile communication between the internal space 3 of said container 1 and that of the enclosure.

The connection device 4 comprises a flange on which the flexible film is attached, said flange delimiting the through-opening of the flexible film, and means of connection to the complementary connection device of the enclosure. According to the invention, the flange is constituted by two pieces distinct from each other, a first piece forming a so-called external sleeve 5 and a second piece forming a so-called internal sleeve 6, between which the flexible film extends.

The connection device 4 further comprises a removable door 7 attached to the flange so as to close the through-opening. Advantageously, the flange and the door 7 are attached to one another by means of notches and lugs respectively borne by the internal sleeve 6 and the door 7. The flange thus defines an assembly flange of the flexible film to the door.

In the illustrated embodiment, the internal sleeve 6 comprises a notched zone 64 adjacent to the bearing recess 61 arranged to cooperate with a complementary notching 54 provided on the inner face 50 of the external sleeve 5.

According to an advantageous configuration illustrated in FIG. 4, the external sleeve 5 comprises a lower skirt 10 comprising longitudinal slots 11 extending from the lower end edge of said sleeve. These longitudinal slots 11 are advantageously evenly distributed over the periphery of said sleeve. They thus delimit elastic tabs 12 capable of exerting a uniform clamping force over the entire outer periphery of the internal sleeve 6 when the external sleeve 5 is mounted on the internal sleeve 6. The elastic tabs 12 comprise means of reciprocal association with clamping means, described below, and the internal sleeve 6, respectively. In the illustrated example, the means of reciprocal association with the clamping ring consist of a thread 53 and a notching 54. The clamping means are arranged to grip the parts of the external sleeve 5 and of the internal sleeve 6 between which the flexible film 2 is interposed. In the illustrated example, the clamping means are in the form of an external clamping ring comprising an internal thread 90 with a shape complementary to a thread 53 provided on the outer face 52 of the external sleeve 5.

In the illustrated example, the external sleeve 5 comprises, at the upper periphery, an arrangement of lugs forming the connection means to the complementary connection device of the enclosure.

The container 1 further comprises a first annular seal 8 housed in a peripheral groove 51 formed on the inner face 50 of the external sleeve 5 and the outer face 60 of the internal sleeve 6. As shown in FIG. 3, the flexible film 2 is kept gripped between the annular seal 8 and the internal sleeve 6. In order to improve the retention of the flexible film 2 between the two sleeves constituting the assembly flange, the internal sleeve 6 comprises an outer face provided with a bearing recess 61 located opposite the peripheral groove 51 of the external sleeve 5. Thus, when the external sleeve 5 is clamped on the internal sleeve 6, the annular seal 8 crushes the flexible film 2 at the bearing recess 61, ensuring improved engagement of the flexible film 2.

The container 1 further comprises a second annular seal 13 that is borne by the flange. When the door is in the position closing off the through-opening, the annular seal 13 is housed in the space delimited by the external sleeve 5, the internal sleeve 6 and the door 7. Advantageously, the annular seal 13 has a cross-section of shape matching the area in which it is housed. In the illustrated embodiment, the annular seal 13 has an L-shaped section.

Figure 5:
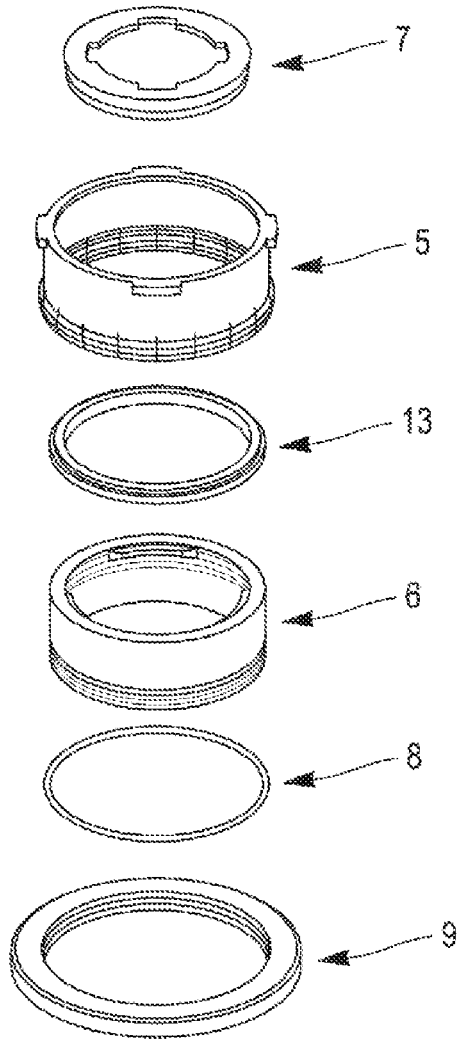
FIG. 5 shows an exploded view of the connection device of the container of FIG. 1.

Due to the arrangement of its component elements, the connection device is assembled by simple clipping of the elements according to the stack illustrated in FIG. 5. To make the container 1, the part of the flexible film located on the side of the through-opening will be arranged so as to be placed between the external sleeve 5 and the internal sleeve 6. The clamping will be effective by clamping the ring 9 on the external sleeve 6, causing the tabs 12 to be gripped against the internal sleeve 6. The flexible film 2 may be disassembled by unscrewing the clamping ring 9 and unclipping the external sleeve 5 from the internal sleeve 6.

Figure 6:
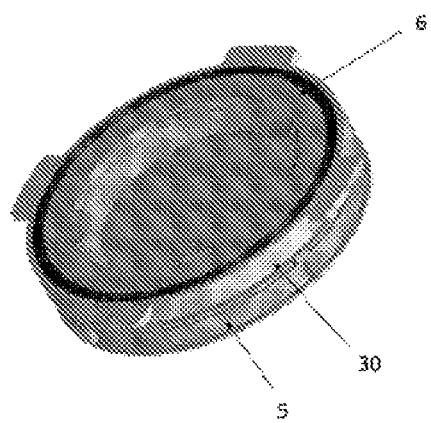
FIG. 6 shows a top perspective view of a connection device of the container according to another embodiment of the invention.
Figure 7:
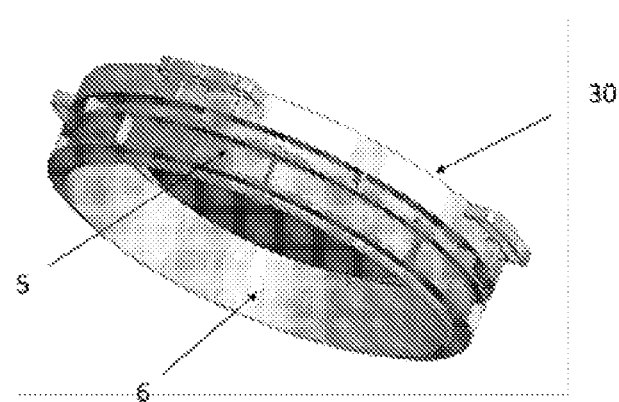
FIG. 7 shows a bottom perspective view of the connection device of FIG. 6.

In the embodiment that has just been described, the external sleeve 5 jointly ensures the function of keeping the flexible film 2 on the internal sleeve 6, and thus maintaining its assembly to the associated door 7, and the function of connection to the connection device fitted to an enclosure. FIG. 6 and following illustrate another embodiment of a container according to the invention in which the connection function to the complementary connection device is ensured, no longer directly by the external sleeve 5, but by an additional piece that will be described later.

As in the previously described variant, the assembly flange of the door 7 to the flexible film 2 consists of an external sleeve 5 and an internal sleeve 6 on which the door 7 is mounted, the flexible film 2 being kept gripped between these two sleeves. The external sleeve 5, which has an axial length less than that of the internal sleeve 6, is sized to encircle the lower part of the internal sleeve 6.

Advantageously, the external sleeve 5 is mounted on the internal sleeve 6 by clipping. To do this, the external sleeve 5 comprises an annular groove 15 arranged to engage on a first circumferential fin 20 of complementary shape provided on the outer face of the internal sleeve 6.

Figures 10, 11:
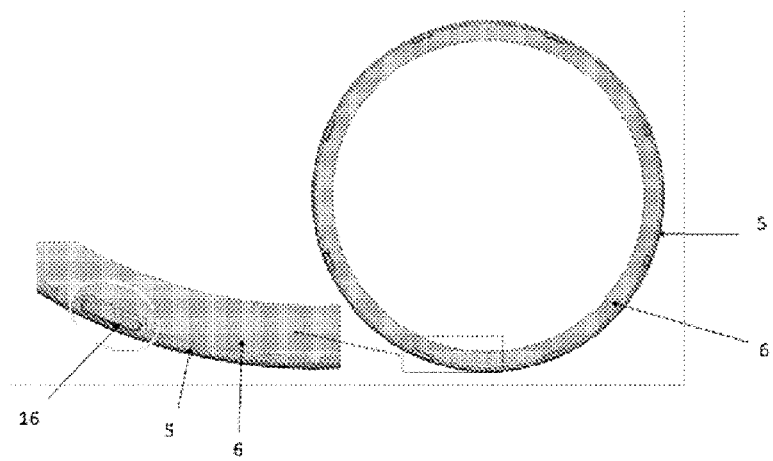
FIG. 10 shows a top sectional view along axis XX of the connection device of FIG. 9.
FIG. 11 shows a detail view of FIG. 10.

The external sleeve 5 further comprises clips 16 cooperating, when said sleeve is clipped onto the internal sleeve 6, with a complementary imprint made on the internal sleeve 6 (FIGS. 10 and 11). The clips 16 thus maintain the axial position of the external sleeve 5 on the internal sleeve 6 on the one hand and maintain the angular position of the external sleeve 5 on the internal sleeve 6 on the other hand. They thus provide axial and angular indexing of the external sleeve 5 on the internal sleeve 6.

Figures 8, 9:
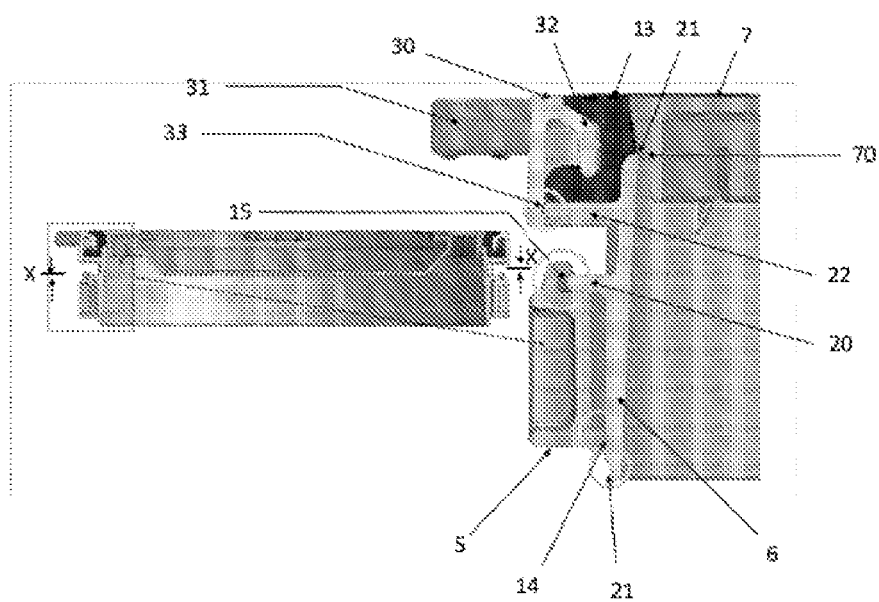
FIG. 8 shows a view in axial section of the connection device of FIG. 6.
FIG. 9 shows a detail view of FIG. 8.

In order to ensure that the film is kept gripped between the two sleeves 5, 6 on the one hand and to ensure the sealing of the external sleeve 5 with the flexible film 2 gripped between the two sleeves on the other hand, the external sleeve 5 has an inner peripheral face provided with a circumferential gadroon 14 arranged to define, with the outer peripheral face of the internal sleeve 6, a compression zone of the film portion 20 engaged between the sleeves (FIGS. 8 and 9). The shapes of the external 5 and internal 6 sleeves are nominally defined so that the gadroon 14 present on the external sleeve 5 interferes with the internal sleeve 6. Pressed and exerting a radial force on the outer peripheral face of the internal sleeve 6, the gadroon 16 acts as a seal. In the illustrated embodiment, the internal annular part 7 comprises a single gadroon 14 located at the lower end of the external sleeve 5 and extending over the entire circumference of the inner peripheral face of said sleeve. It is of course obvious that several different gadroons can be provided without departing from the scope of the invention.

In addition to the external sleeve 5, the internal sleeve 6 is provided in the upper part with a collar 30 bearing the connection means 31 to the complementary connection device of the enclosure. The collar 30 thus forms a so-called connecting flange. The collar 30 will subsequently be referred to as a connecting collar or flange.

The connecting collar 30 is mounted at the upper end of the internal sleeve 6 by joint clipping with the seal 13 and the door 7 (FIGS. 8 and 9). The connecting collar 30 comprises an internal circumferential extension 32 sized to engage forcibly in the cavity of the seal 13. It also advantageously comprises, in the lower part, a hollow annular cavity 33 in which a second circumferential fin 22 of the internal sleeve 6 engages.

Figures 12, 13:
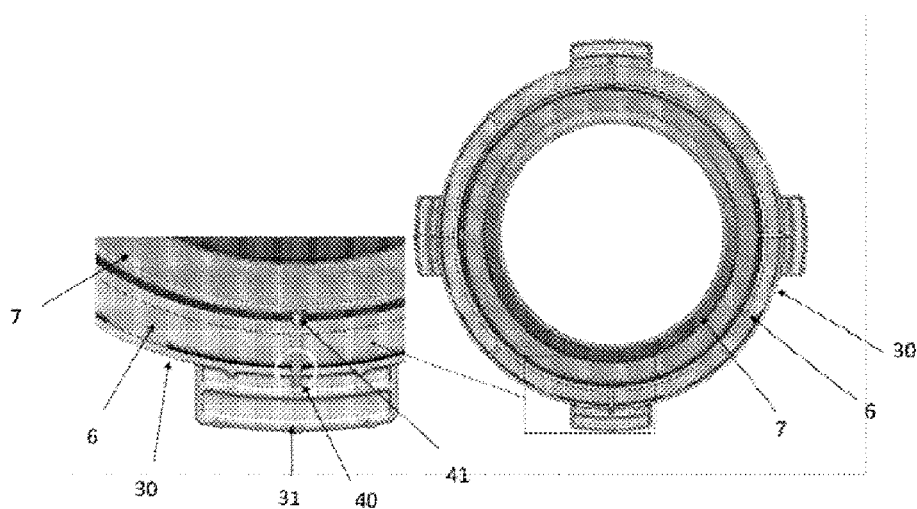
FIG. 12 shows a bottom sectional view along axis XX of the connection device of FIG. 9.
FIG. 13 shows a detail view of FIG. 12.
Figures 14, 15:
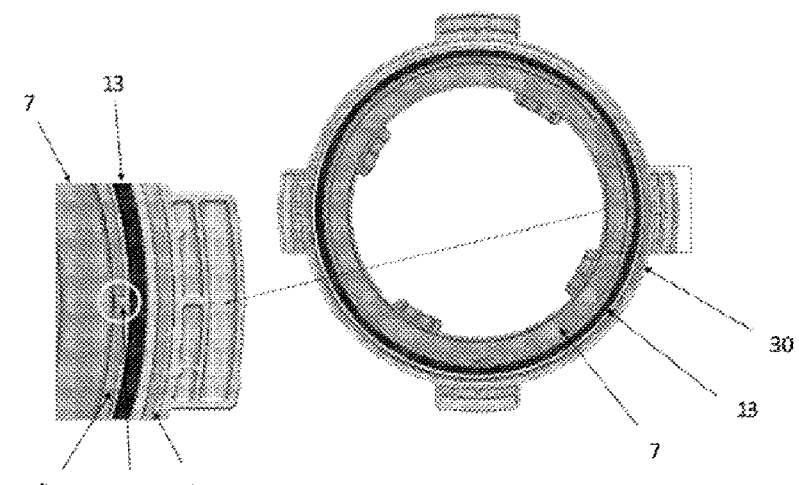
FIG. 14 shows a top view of the connection device of FIG. 6.
FIG. 15 shows a detail view of FIG. 14.

Advantageously, the container comprises first indexing means 40 of the connecting collar 30 with the internal sleeve 6, illustrated in FIGS. 12 and 13, and second indexing means 41 of the door 7 with the internal sleeve 6, illustrated in FIGS. 14 and 15; in the illustrated example, the first and second indexing means are radial fingers.

In this variant, the clamping ring and the associated seal 8 are no longer necessary to respectively ensure the maintenance of the flexible film 2 and the sealing of the assembly, these functions being jointly ensured by the external sleeve 5 mounted forcibly on the internal sleeve 6, and the associated gadroon. In order to reinforce the sealing of the assembly ensured by the gadroon 14, the flexible film 2 is advantageously thermoformed beforehand on the internal sleeve 6 so as to form a sealed annular contact line on the surface of the internal sleeve 6. The thermoforming will be carried out at the limit of the weld of the flexible film on the internal sleeve 6 in order to ensure satisfactory attachment of the film while preserving its integrity. The contact line is produced so as to be located above the gadroon 14 when the external sleeve 5 is fitted onto the internal sleeve 6. Thus, during assembly, the flexible film 2 is pinched and the force is maintained by the elasticity of the two rings, which have deformed under the force linked to the displacement induced by the interference defined between the gadroon 14 and the internal sleeve 6.

Advantageously, the internal sleeve 6 comprises an external chamfer 21, of conical shape, made at the lower end of said sleeve (FIGS. 8 and 9) to facilitate the threading and the sliding of the flexible film 2 on the internal sleeve 6. Moreover, and as in the example previously described, the internal sleeve 6 and the door 7 are respectively provided with notches 70 and lugs allowing them to be assembled by clipping.

The flexible film 2 and the connection device 4 are advantageously made of a bacteriostatic material. The seals 8 and 13 are made of a silicone material or other materials minimizing remanence phenomena. Provision may also be made for the seals to be made of a bacteriostatic material.

The invention is described in the foregoing by way of example. It is understood that a person skilled in the art is in a position to produce various variant embodiments of the invention without thereby departing from the scope of the invention.

The invention claimed is:

1. A sealed container comprising:
   a flexible film arranged to define an internal space and a through-opening;
   a door closing off the through-opening;
   a sealed connection device arranged to allow the flexible film to be connected to a complementary connection device of a sterile enclosure by providing sterile communication between the internal space of said container and that of the enclosure, the connection device comprising:
      an assembly flange for assembling the door to the flexible film; and
      means for connection to the complementary connection device of the enclosure, said assembly flange delimiting the through-opening of the flexible film, characterized in that the assembly flange is constituted by two pieces distinct from each other, respectively forming an external sleeve and an internal sleeve on which the door is mounted; and
   a means of ensuring the sealing of the external sleeve with the flexible film gripped between the external sleeve and the internal sleeve, said means of ensuring the sealing being an annular seal housed in an internal peripheral groove of the external sleeve to bear on the internal sleeve, said flexible film being gripping between the annular seal and the internal sleeve;
      wherein the external sleeve is mounted clipped onto the internal sleeve.

2. The sealed container according to claim 1, characterized in that the internal sleeve is surrounded in the lower part by the external sleeve and in the upper part by a connecting collar arranged to ensure the connection to the complementary connection device of the enclosure, the collar forming said connection means.

3. The sealed container according to claim 2, characterized in that it comprises first means for indexing the connecting collar with the internal sleeve.

4. The sealed container according to claim 3, characterized in that it comprises second means for indexing the door with the internal sleeve.

5. The sealed container according to claim 1, characterized in that the connection means to the complementary connection device of the enclosure are formed integrally with the external sleeve.

6. The sealed container according to claim 5, characterized in that it comprises means for clamping the external sleeve on the internal sleeve arranged to grip the parts of the external sleeve and of the internal sleeve between which the flexible film is interposed.

7. The sealed container according to claim 5, characterized in that it comprises an annular seal housed in an internal peripheral groove of the external sleeve, the flexible film extending between the annular seal and the internal sleeve.

8. The sealed container according to claim 5, characterized in that the external sleeve comprises a lower skirt comprising longitudinal slots extending from the lower end edge of the external sleeve and evenly distributed over the periphery of said sleeve so as to form elastic tabs capable of exerting a clamping force on the internal sleeve.

9. The sealed container according to claim 1, characterized in that it comprises means for clamping the external sleeve on the internal sleeve arranged to grip the parts of the external sleeve and of the internal sleeve between which the flexible film is interposed.

10. The sealed container according to claim 1, characterized in that the internal sleeve comprises a face provided with a bearing recess located opposite the peripheral groove of the external sleeve.

11. The sealed container according to claim 10, characterized in that the internal sleeve comprises a notched zone adjacent to the bearing recess arranged to cooperate with a complementary notching provided on the inner face of the external sleeve.

12. The sealed container according to claim 1, characterized in that the external sleeve comprises a lower skirt comprising longitudinal slots extending from the lower end edge of the external sleeve and evenly distributed over the periphery of said sleeve so as to form elastic tabs capable of exerting a clamping force on the internal sleeve.

13. The sealed container according to claim 12, characterized in that the elastic tabs comprise means of reciprocal association with a clamping means.

14. The sealed container according to claim 1, characterized in that the flange comprises an annular seal having a substantially L-shaped section housed in an area delimited by the external sleeve, the internal sleeve and the door.

15. The sealed container according to claim 1, characterized in that the flexible film and the connection device are made of a bacteriostatic material.

* * * * *